United States Patent
Wiklof

(10) Patent No.: US 7,534,205 B2
(45) Date of Patent: May 19, 2009

(54) METHODS AND APPARATUSES FOR SELECTING AND DISPLAYING AN IMAGE WITH THE BEST FOCUS

(75) Inventor: Christopher A. Wiklof, Everett, WA (US)

(73) Assignee: Microvision, Inc., Redmond, WA (US)

( * ) Notice: Subject to any disclaimer, the term of this patent is extended or adjusted under 35 U.S.C. 154(b) by 429 days.

(21) Appl. No.: 11/364,628

(22) Filed: Feb. 27, 2006

(65) Prior Publication Data
US 2007/0203394 A1    Aug. 30, 2007

(51) Int. Cl.
*A61B 1/06* (2006.01)

(52) U.S. Cl. .................. 600/173; 600/109; 600/160

(58) Field of Classification Search ............. 600/109, 600/160, 163, 167, 168, 173, 178, 476–478; 348/65, 68, 74; 250/227.26; 359/202, 204
See application file for complete search history.

(56) References Cited

U.S. PATENT DOCUMENTS

| | | | |
|---|---|---|---|
| 6,485,413 B1 * | 11/2002 | Boppart et al. ............. 600/160 |
| 6,607,489 B2 * | 8/2003 | Hoctor et al. .............. 600/443 |
| 7,435,217 B2 * | 10/2008 | Wiklof ..................... 600/173 |
| 7,448,995 B2 * | 11/2008 | Wiklof et al. .............. 600/173 |
| 2004/0073087 A1 * | 4/2004 | Glukhovsky et al. ......... 600/109 |
| 2005/0025368 A1 * | 2/2005 | Glukhovsky ............... 382/236 |

* cited by examiner

*Primary Examiner*—John P Leubecker
*Assistant Examiner*—Samuel Candler
(74) *Attorney, Agent, or Firm*—Kevin D. Wills

(57) ABSTRACT

Methods and apparatuses for selecting and displaying an image with the best focus are disclosed. In one aspect, a method of displaying a captured image includes capturing a plurality of images of a field of view (FOV) using an image capture device, selecting one of the images having the best focus, and displaying the selected image on the image capture device. In another aspect, a method of displaying a captured image includes capturing a plurality of images of a FOV, dividing each of the images into a plurality of regions, and comparing corresponding regions from each of the images. The regions having the best focus are selected. A composite image is constructed formed from the regions with the best focus and the composite image is displayed. Image capture devices configured to effect the above methods are also disclosed.

12 Claims, 5 Drawing Sheets

METHODS AND APPARATUSES FOR SELECTING AND DISPLAYING AN IMAGE WITH THE BEST FOCUS

TECHNICAL FIELD

This invention relates to image capture devices and, more particularly, to scanned beam imagers and scanned beam endoscopes configured to select and display an image with the best focus.

BACKGROUND

Scanned beam imagers are a promising imaging technology that function by scanning a beam of light over a FOV, collecting the reflected light from the FOV into an optical sensor, and forming a digital image based on the characteristics of the reflected light. Scanned beam imagers may offer a greater range and depth of field, reduced motion blur, enhanced resolution, extended spectral response, reduced cost, reduced size, lower power consumption, and improved shock and vibration tolerance.

FIG. 1 shows a block diagram of a scanned beam imager 10 in accordance with the prior art. The scanned beam imager 10 includes a light source 12 operable to emit a beam of light 14. A scanner 16 is positioned to receive and scan the beam 14 across a FOV 11 as a scanned beam 18 having a fixed beam waist distance. Instantaneous positions of the scanned beam of light 18 are designated as 18a and 18b. The scanned beam 18 sequentially illuminates spots 20 in the FOV at positions 20a and 20b, respectively. While the scanned beam 18 illuminates the spots, a portion of the illuminating scanned beam 18 is reflected (e.g., specular reflected light and diffuse reflected light also referred to as scattered light), absorbed, refracted, or otherwise affected according to the properties of the object or material at the spots to produce reflected light 22a and 22b. A portion of the reflected light 22a and 22b is received by one or more detectors 24, which generates electrical signals corresponding to the amount of light energy received. The electrical signals drive a controller 26 that builds up a digital representation of the FOV and transmits it for further processing, decoding, archiving, printing, display, or other treatment or use via interface 28.

One promising application for a scanned beam imager is in an endoscope.

Endoscopes are typically flexible or rigid devices that have an endoscope tip including a viewing device. The endoscope tip is inserted in a body cavity for viewing anatomical features of the cavity. The viewing device is typically a device, such as a video camera or a scanned beam imager. Electronic or optical signals associated with the images taken by the viewing device are sent up a flexible tube to a console for display and viewing by a medical professional such as a doctor or nurse.

Scanned beam endoscopes that employ scanned beam imager technology are a fairly recent innovation, and an example of a scanned beam endoscope is disclosed in U.S. patent application No. 10/873,540 ("'540 Application") entitled SCANNING ENDOSCOPE, hereby incorporated by reference and commonly assigned herewith.

The scanned beam endoscope disclosed in the '540 Application scans a beam across a FOV having a fixed beam waist distance from the distal end of its endoscope tip.

While the scanned beam imager 10 and the scanned beam endoscope are effective imaging devices, they have a limited depth of field because the beam waist distance of the scanned beam 18 of the scanned beam imager 10 and the beam waist distance of the scanned beam of the scanned beam endoscope are fixed. However, superior resolution for a captured image is obtained when the working distance is approximately equal to the beam waist distance. Since the scanned beam imager 10 and the scanned beam endoscope have a fixed beam waist distance and, consequently a limited depth of field, the captured image may not have the quality of resolution desired by the user depending upon the working distance the image capture device is from the FOV or a portion of the FOV being imaged.

Therefore, it would be desirable to provide an image capture device and method, which may be implemented in an endoscope, that can capture higher resolution images of a FOV.

SUMMARY

Methods and apparatuses for selecting and displaying an image with the best focus are disclosed. In one aspect, a method of displaying a captured image and an image capture device such as an endoscope configured to effect such a method is disclosed. The method includes capturing a plurality of images of a field of view (FOV) using an image capture device, selecting one of the images having the best focus, and displaying the selected image on a display.

In another aspect, a method of displaying a composite image formed of regions of best focus from a plurality of captured images and an image capture device such as an endoscope configured to effect such a method is disclosed. The method includes capturing a plurality of images of a FOV, dividing each of the images into a plurality of regions, and comparing corresponding regions from each of the images. The regions having the best focus are selected. A composite image is constructed formed from the regions with the best focus and the composite image is displayed.

DETAILED DESCRIPTION OF THE EMBODIMENTS

Apparatuses and methods for image capture devices configured to select and display an image with the best focus are disclosed. Many specific details of certain embodiments are set forth in the following description and in FIGS. 2 through 4 in order to provide a thorough understanding of such embodiments. One skilled in the art, however, will understand that there may be additional embodiments, or that the disclosed embodiments may be practiced without several of the details described in the following description.

Figure 1:
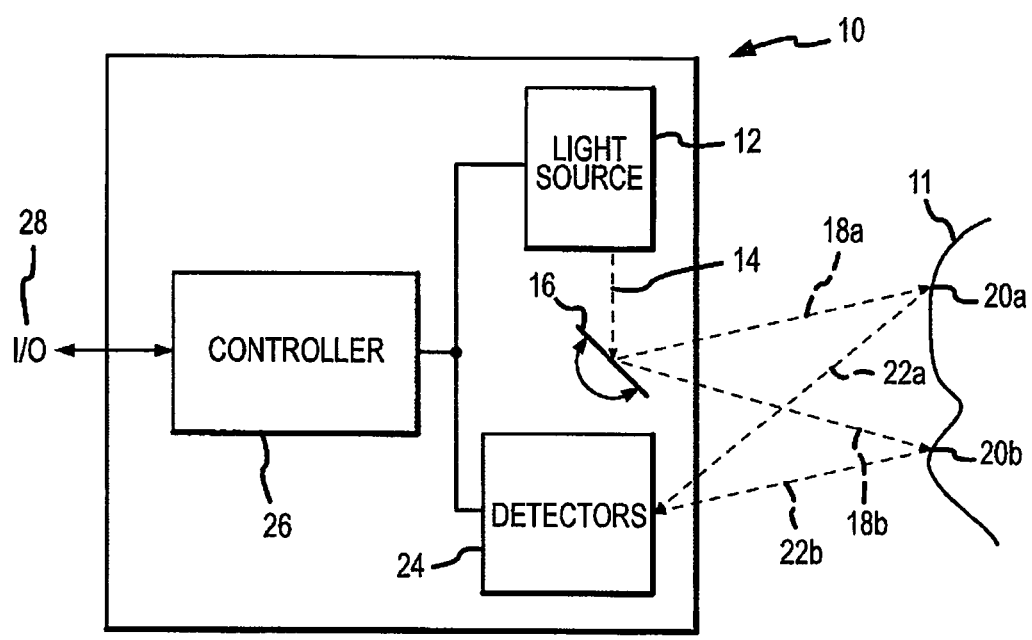
FIG. 1 is a block diagram of a scanned beam imager in accordance with the prior art.
Figure 2:
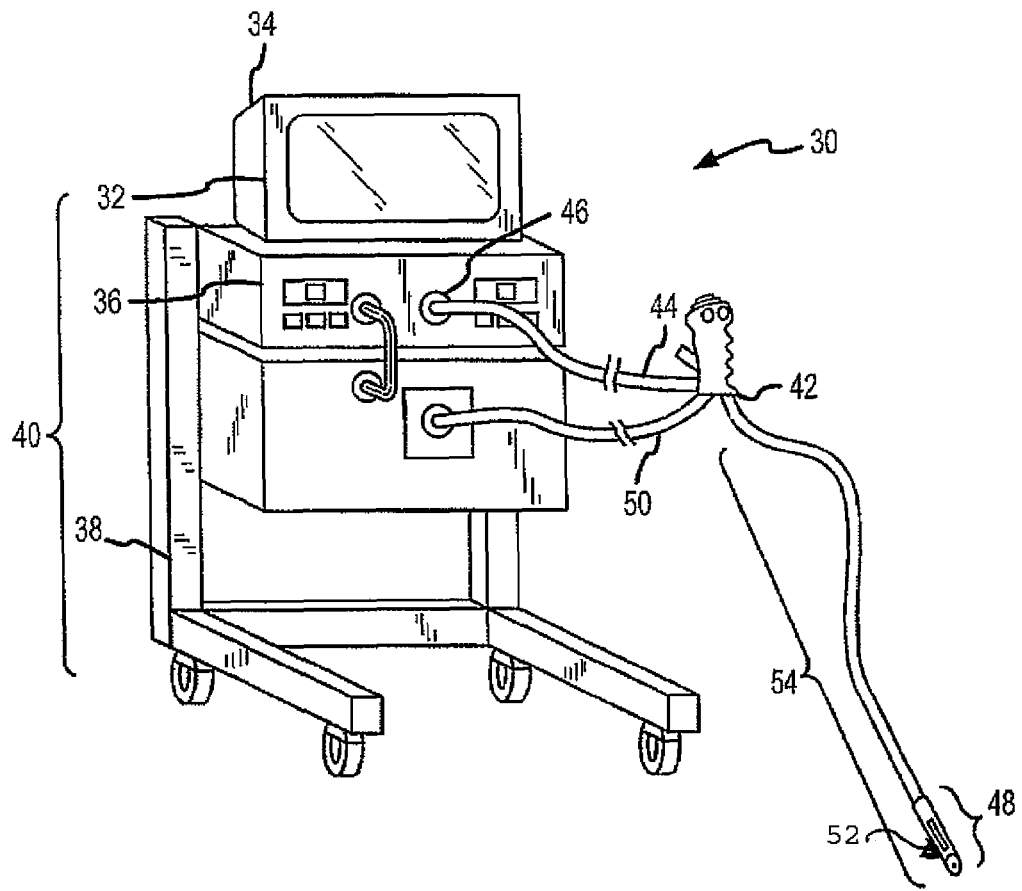
FIG. 2 is schematic drawing of a scanned beam endoscope in accordance with one embodiment that may be used for implementing the methods of FIGS. 3 and 4.

FIG. 2 shows one embodiment of a scanned beam endoscope 30 suitable for implementing methods described below in FIGS. 3 and 4. The scanned beam endoscope 30 includes a controller 32 and monitor 34, both of which may be mounted on a cart 38. The controller 32 may include components such as, a scanner controller 36, one or more light sources 37, memory 50, and a video processor and controller 52 configured to control the operation of such components of the controller 32.

The controller 32 communicates with a handpiece 42 through an external cable 44, which is connected to the console 40 via connector 46, and further controls the operation of the various components of the endoscope 30. An endoscope tip 54 is operably coupled to the handpiece 42. The endoscope tip 54 may be formed of a flexible or rigid housing 54 that encloses components of a distal tip 48, such as optical fibers and electrical wiring.

The distal tip 48 includes a viewing device 52 for viewing anatomical features of a cavity that the distal tip 48 is positioned within responsive to user input via the handpiece 42. The viewing device 52 may be an image capture device, such as a scanned beam device that operates in conjunction with the controller 32 as a scanned beam imager. The scanned beam device may include one or more illumination optical fibers coupled to a light source in the controller 32, a MEMS scanner (not shown) for scanning the light output from the illumination optical fiber (not shown) as a scanned beam, and detection optical fibers (not shown) for collecting reflected light from the FOV being viewed and transmitting the collected light to an optical-electrical converter that converts the optical signals to an electrical signal with which the controller 32 generates an image for display on the monitor 34 characteristic of the FOV. The distal tip 48 may be configured to scan a plurality of beams across the FOV having different respective beam waist distances. Various embodiments for the distal tip 48 of the endoscope tip 54 that are configured to simultaneously or selectively scan beams across the FOV having different respective beam waist distances are disclosed in application Ser. No. 11/679,105, filed on Feb. 26, 2007, entitled SCANNED BEAM IMAGER AND ENDOSCOPE CONFIGURED FOR SCANNING BEAMS OF SELECTED BEAM C SHAPES AND/OR PROVIDING MULTIPLE FIELD-OF-VIEWS. For example, the distal tip 48 may include a plurality of optical fibers associated with scanned beams having different beam waist distances. The methods disclosed in FIGS. 3 and 4 may also be implemented on other pixilated image capture devices such as digital cameras.

In operation, the distal tip 48 is inserted within a body cavity. Responsive to user input via the handpiece 42, the controller 32 effects scanning of one or more beams from the distal tip 48 over the FOV. Reflected light from an interior surface of the body cavity may be collected by the distal tip 48. A signal representative of an image of the internal surfaces is sent from the distal tip 48 to the console 40 for viewing on the monitor 34 and diagnosis by a medical professional.

Figure 3:
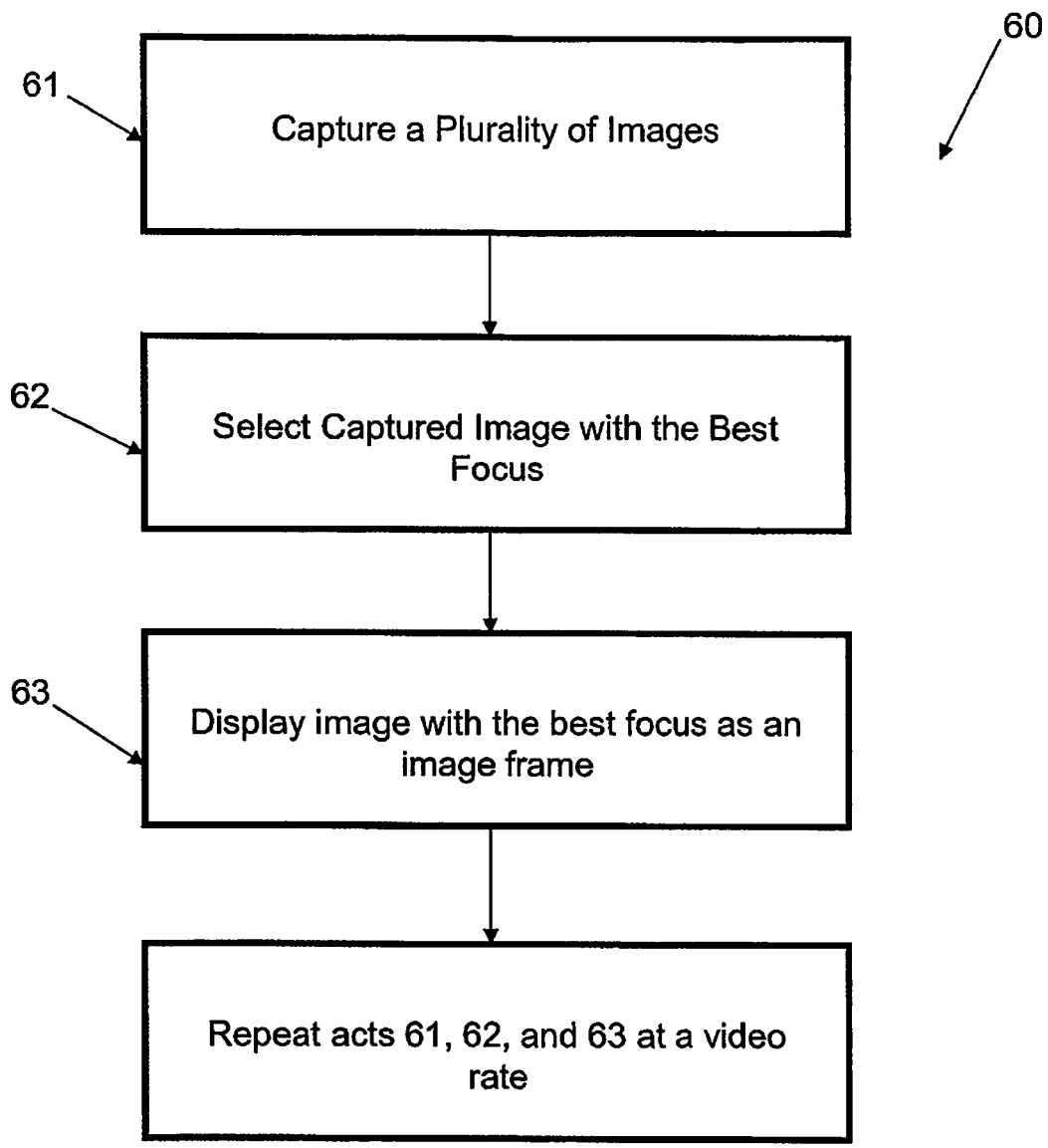
FIG. 3 is a flow diagram of a method for selecting and displaying an image with a best focus from a plurality of captured images in accordance with one embodiment.

FIG. 3 is a flow chart of a method 60 for selecting and displaying an image with a best focus from a plurality of captured images in accordance with one embodiment. The method 60 may be implemented using a variety of image capture devices, such as the scanned beam endoscope 30 with the controller 32 thereof being configured to execute the method 60. In practice, an image capture device is positioned proximate a FOV such as by positioning the distal tip 48 of the scanned beam endoscope 30 within a body cavity. In act 61, a plurality of images of the FOV are captured. In one embodiment, the plurality of images of the FOV are captured by scanning a first beam having a first beam waist distance across the FOV and scanning at least a second beam having a second beam waist distance across the FOV. The reflected light from the FOV associated with the first and second beams are collected and processed to define first and second captured images. In some embodiments, the plurality of images may be captured simultaneously or substantially simultaneously. For example, if first and second beams having different beam waist distances are scanned simultaneously or substantially simultaneously across the FOV, the optical signals of the images associated with each of the first and second beams may be determined by wavelength, time, or frequency multiplexing. In yet another embodiment, the first and second beams may be sequentially scanned and each of the captured images may be sequentially captured.

In act 62, the captured image with the best focus is selected from the first and second images. The determination of which captured image has the best focus may be determined using a variety of different techniques. In various embodiments, the captured image with the best focus may be determined by comparing the apparent range of brightness from each captured image, comparing the RMS feature size from each captured image, comparing the contrast from each captured image, or comparing the edge definition of each captured image. Comparing the apparent range of brightness from each captured image relies upon the relationship that brightness is inversely proportional to the square of the working distance. Thus, the average brightness of each captured image may be correlated to the approximate working distance. When the aforementioned embodiment of a scanned beam endoscope or imager configured to scan multiple beams each having different beam waist distances is used to implement the method 60, the captured image captured from a working distance that is closest to the beam waist distance of the scanned beam used to generate it is selected.

Implementation of comparing the RMS feature size to determine best focus is very similar to the apparent range of brightness method. In the RMS feature size method, the average size of features of FOV (e.g., the average size of features observed on the inside of a body cavity such as a human intestine) is proportional to the inverse of the working distance. Accordingly, the RMS feature size of each captured image may be correlated to the approximate working distance. Again, when the aforementioned embodiment of a scanned beam endoscope or imager configured to scan multiple beams each having different beam waist distances is used to implement the method 60, the captured image captured from a working distance that is closest to the beam waist distance of the scanned beam used to generate it is selected. Another technique for determining which particular captured image has the best focus compares the contrast of each captured image and the captured image with the greatest contrast may be selected. Yet another technique for determining which particular captured image has the best focus compares the edge definition of each captured image and the captured image with the greatest edge definition is selected.

In act 63, the captured image with the best focus is displayed as an image frame. The captured image with the best focus may be displayed on a viewing monitor, such as the monitor 34 in the case of the scanned beam endoscope 30. The acts 61, 62, and 63 may be continuously repeated at a video rate to display a video image with the captured images having the best focus being continuously displayed.

Figure 4:
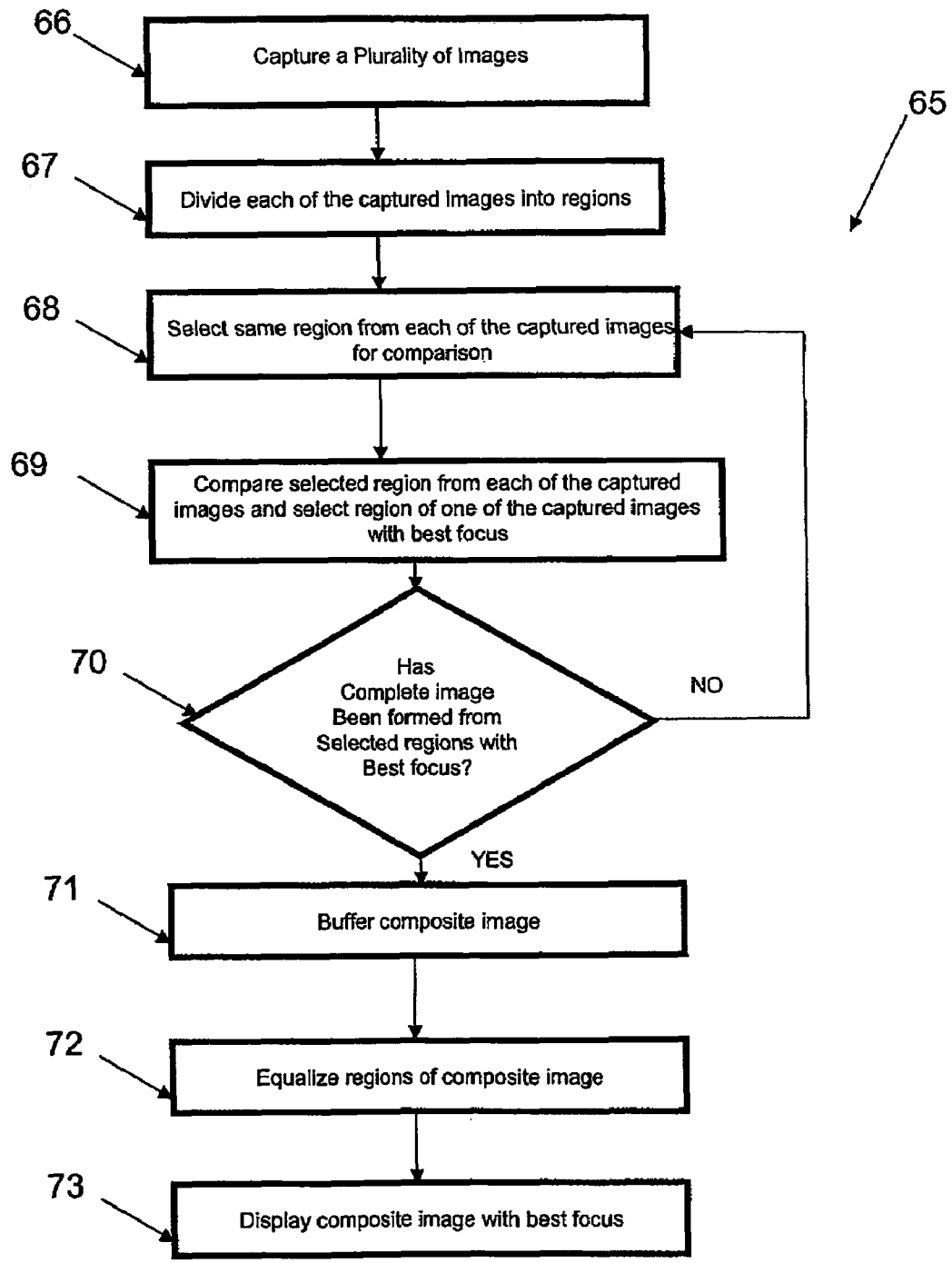
FIG. 4 is a flow diagram of a method for selecting and displaying a composite image formed of regions of best focus from a plurality of captured images in accordance with one embodiment.

FIG. 4 is a flow chart of a method 65 for selecting and displaying a composite image formed of regions of best focus from a plurality of captured images in accordance with one embodiment. Again, the method 65 may be implemented using a variety of image capture devices, such as the scanned beam endoscope 30 with the controller 32 thereof being configured to execute the method 65. In act 66, a plurality of images of the FOV are captured. The plurality of images may be captured in the same manner as performed in act 61 of the method 60 shown in FIG. 3. In act 67, each of the captured images is divided into a plurality of regions. In act 68, the same region from each of the captured images is selected for comparison with each other. In act 69, the region selected from each of the captured images in act 68 is compared with each other and the region of one of the captured images having the best focus is selected. As previously discussed when describing the method 60 illustrated in FIG. 3, the best focus may be determined in act 70 by comparing the apparent brightness, RMS feature size, contrast, or edge definition of the region being evaluated. The acts 68 and 69 may be repeated on the remaining regions of each of the captured images that have not been compared with each other until a complete composite image is buffered. The composite image is formed from regions selected from the plurality of captured having the best focus or quality.

With continued reference to FIG. 4, in act 71, the composite image formed of the regions with the best focus is buffered, for example, in the memory 50 of the scanned beam endoscope 30. In act 72, the buffered composite image is equalized such that the apparent brightness of each of the regions that define the composite image is adjusted to reduce the visibility of the different regions. In act 73, the composite image formed of regions of best focus selected from different captured images is displayed such as on the monitor 34 in the case of the scanned beam endoscope 30. The process of generating the composite image may be repeated at a video rate.

Figure 5:
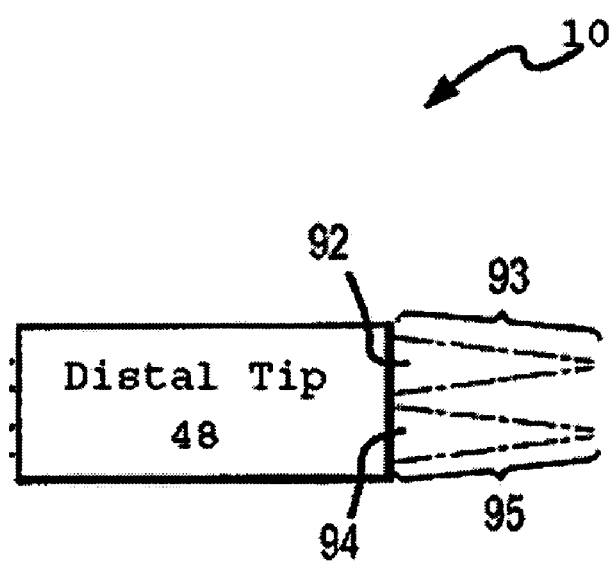
FIG. 5 is a block diagram of one embodiment of a scanned beam imager configured to scan beams having different beam waist distances.

FIG. 5 is a scanned beam imager 10 for selecting and displaying an image with a best focus from a plurality of captured images in accordance with one embodiment. The scanned beam imager 10 may be implemented using a variety of image capture devices, such as the scanned beam endoscope 30 with the controller 32. In practice, an image capture device is positioned proximate a FOV such as by positioning the distal tip 48 of the scanned beam endoscope 30 within a body cavity. In one embodiment, a plurality of images of the FOV are captured by scanning a first beam 92 having a first beam waist distance 93 across the FOV and scanning at least a second beam 94 having a second beam waist distance 95 across the FOV. In an embodiment, first beam waist distance 93 is not equal to second waist beam distance 95.

From the foregoing it will be appreciated that, although specific embodiments of the invention have been described herein for purposes of illustration, various modifications may be made without deviating from the spirit and scope of the invention. For example, while the methods and apparatuses have been described using scanned beam imagers and scanned beam endoscopes, the methods disclosed herein are applicable for use with a variety of other pixilated-type image capture devices. Accordingly, the invention is not limited except as by the appended claims.

What is claimed is:

1. A method of displaying a captured image, comprising:
capturing a plurality of images of a field of view (FOV) using an image capture device;
selecting one of the images having the best focus;
displaying the selected image on a display;
scanning a first beam having a first beam waist distance across the FOV and scanning at least a second beam having a second beam waist distance that is not equal to the first beam waist distance across the FOV; and
collecting reflected light from the FOV associated with the first and at least a second scanned beams.

2. The method of claim 1 wherein the act of scanning a first beam having a first beam waist distance across the FOV and scanning at least a second beam having a second beam waist distance that is not equal to the first beam waist distance across the FOV comprises scanning the first and at least a second beams across the FOV substantially simultaneously.

3. The method of claim 1 wherein the act of scanning a first beam having a first beam waist distance across the FOV and scanning at least a second beam having a second beam waist distance that is not equal to the first beam waist distance across the FOV comprises scanning the first and at least a second beams across the FOV sequentially.

4. An endoscope, comprising:
an endoscope tip including a viewing device operable to provide signals characteristic of a field of view (FOV);
a display; and
a controller operably coupled to the endoscope tip, the controller being configured to:
effect capture of a plurality of images of the FOV corresponding to the signals with the viewing device;
select one of the images having the best focus; and
display the selected image on the display, viewing device comprises a scanned beam device operable to scan a first beam having a first beam waist distance across the FOV and scan at least a second beam having a second beam waist distance that is not equal to the first beam waist distance across the FOV, the scanned beam device is configured to collect reflected light from the FOV associated with the first and at least a second scanned beams.

5. The endoscope of claim 4 wherein the controller is configured to effect scanning the first and at least a second beams across the FOV substantially simultaneously.

6. The endoscope of claim 4 wherein the controller is configured to effect scanning the first and at least a second beams across the FOV sequentially.

7. A method of displaying a captured image, comprising:
capturing a plurality of images of a field of view (FOV), wherein the act of capturing a plurality of images of a FOV comprises:
scanning a first beam having a first beam waist distance across the FOV and scanning at least a second beam having a second beam waist distance that is not equal to the first beam waist distance across the FOV; and
collecting reflected light from the FOV associated with the first and at least a second scanned beams;
dividing each of the images into a plurality of regions;
comparing corresponding regions from each of the images;
selecting the regions having the best focus;
constructing a composite image formed from the regions having the best focus; and
displaying the composite image.

8. The method of claim 7 wherein the act of scanning a first beam having a first beam waist distance across the FOV and scanning at least a second beam having a second beam waist distance that is not equal to the first beam waist distance across the FOV comprises scanning the first and at least a second beams across the FOV substantially simultaneously.

9. The method of claim 7 wherein the act of scanning a first beam having a first beam waist distance across the FOV and scanning at least a second beam having a second beam waist distance that is not equal to the first beam waist distance across the FOV comprises scanning the first and at least a second beams across the FOV sequentially.

10. An endoscope, comprising:
an endoscope tip including a viewing device operable to provide signals characteristic of a field of view (FOV);
a display; and
a controller operably coupled to the endoscope tip, the controller being configured to:
  effect capture of a plurality of images of the FOV characteristic of the signals with the viewing device;
  divide each of the images into a plurality of regions;
  compare corresponding regions from each of the images;
  select the regions of best focus;
  construct a composite image formed from the regions of best focus; and
  display the composite image on the display, wherein the viewing device comprises a scanned beam device operable to scan a first beam having a first beam waist distance across the FOV and scan at least a second beam having a second beam waist distance that is not equal to the first beam waist distance across the FOV, the scanned beam device being configured to collect reflected light from the FOV associated with the first and at least a second scanned beams.

11. The endoscope of claim 10 wherein the controller is configured to effect scanning the first and at least a second beams across the FOV substantially simultaneously.

12. The endoscope of claim 10 wherein the controller is configured to effect scanning the first and at least a second beams across the FOV sequentially.

* * * * *